(12) United States Patent
Garcia et al.

(10) Patent No.: US 11,633,302 B2
(45) Date of Patent: *Apr. 25, 2023

(54) PATIENT INTERFACE DEVICE FOR OPHTHALMIC SURGICAL LASER SYSTEM

(71) Applicant: AMO Development, LLC, Santa Ana, CA (US)

(72) Inventors: Jose L. Garcia, Fremont, CA (US); Roger W. Accurso, Corning, CA (US); Daryl Wong, San Jose, CA (US); Zenon Witowski, Pleasanton, CA (US)

(73) Assignee: AMO Development, LLC, Irvine, CA (US)

( * ) Notice: Subject to any disclaimer, the term of this patent is extended or adjusted under 35 U.S.C. 154(b) by 112 days.

This patent is subject to a terminal disclaimer.

(21) Appl. No.: 17/210,418

(22) Filed: Mar. 23, 2021

(65) Prior Publication Data

US 2021/0205129 A1 Jul. 8, 2021

Related U.S. Application Data

(63) Continuation of application No. 15/796,610, filed on Oct. 27, 2017, now Pat. No. 10,966,864.

(60) Provisional application No. 62/414,605, filed on Oct. 28, 2016.

(51) Int. Cl.
*A61F 9/009* (2006.01)
(52) U.S. Cl.
CPC ........ *A61F 9/009* (2013.01); *A61F 2210/009* (2013.01)

(58) Field of Classification Search
CPC ........................... A61F 9/009; A61F 2210/009
USPC ............................................................. 606/4
See application file for complete search history.

(56) References Cited

U.S. PATENT DOCUMENTS

| | | | |
|---|---|---|---|
| 9,089,401 B2 | 7/2015 | Raksi et al. | |
| 10,966,864 B2 * | 4/2021 | Garcia | A61F 9/009 |
| 2007/0093795 A1 | 4/2007 | Melcher et al. | |
| 2011/0190741 A1 | 8/2011 | Deisinger et al. | |
| 2014/0276673 A1 | 9/2014 | Heitel et al. | |
| 2015/0335479 A1 | 11/2015 | Shibata et al. | |
| 2016/0151203 A1 | 6/2016 | Gooding et al. | |

* cited by examiner

*Primary Examiner* — Aaron F Roane
(74) *Attorney, Agent, or Firm* — Johnson & Johnson Surgical Vision, Inc.

(57) ABSTRACT

Apparatus and method for interfacing an ophthalmic surgical laser system with a patient's eye using a single-piece patient interface (PI). The PI includes a hollow shell, with an applanation lens and a flexible skirt at its lower end. Through channels are formed around the applanation lens to connect the spaces above and below the lens. When the PI is coupled to the laser system and the eye, the upper rim of the shell forms a seal with the laser system and the flexible skirt forms a seal with the eye. A vacuum is applied to the interior of the shell via a vacuum port on the laser system, and the vacuum is communicated to the space enclosed by the applanation lens, the skirt and the eye through the channels around the lens. A magnetic mechanism is also provided to hold the PI shell to the laser system.

8 Claims, 7 Drawing Sheets

PATIENT INTERFACE DEVICE FOR OPHTHALMIC SURGICAL LASER SYSTEM

RELATED APPLICATIONS

This application is a continuation of U.S. patent application Ser. No. 15/796,610, filed Oct. 27, 2017, which claims priority to, and the benefit of, under U.S.C. § 119(e) of U.S. Provisional Application No. 62/414,605, filed on Oct. 28, 2016. The above-referenced applications are incorporated herein by reference in their entireties.

BACKGROUND OF THE INVENTION

Field of the Invention

Embodiments of this invention generally relate to ophthalmic surgical laser systems, and particularly to a patient interface device used to stabilize the patient's eye and to deliver the laser beam to the eye during ophthalmic surgery, as well as related methods.

Description of Related Art

Significant developments in laser technology have led to its application in the field of ophthalmic surgery, and laser surgery has become the technique of choice for ophthalmic surgical applications. Ophthalmic surgery is a precision operation and requires precise coupling between the surgical tool (i.e., the laser beam) and the region to be surgically altered (i.e., a portion of the patient's eye). Movement of the eye with respect to the intended focal point of the laser beam can lead to non-optimal results and could even result in permanent damage to tissue within the eye. Given that eye movement is often the result of autonomic reflex, techniques have been developed in an attempt to stabilize the position of a patient's eye with respect to an incident laser beam.

Mechanical stabilization devices, referred to as patient interfaces (PI), have been developed for coupling the patient's eye to the laser system. A PI has a component that directly contacts the eye, and engages and stabilizes the eye; meanwhile, the PI is attached to the laser system, so that the laser beam can be aligned to the eye. Some PIs are described in commonly-owned U.S. Pat. Appl. No. 2014/0276673. FIGS. 1-3B of this application shows a PI which includes an ocular attachment ring that couples to the eye, a gripper device, and a lens cone with an applanation lens which is used to establish an appropriate optical path alignment between the cornea and a laser optical path. The lens cone and the ocular attachment ring are interfaced together by the gripper device. The ocular attachment ring has a skirt that forms an annular channel between the eye and the skirt, and a vacuum can be applied to the annular channel via tubing that connect the ocular attachment ring to a vacuum source. FIGS. 4-5A of the above application show another PI with a fluid-filled bladder which can be placed on the patient's eye. FIGS. 6-10 of the above application show yet another PI where a fluid fills a space between the PI and the eye surface.

U.S. Pat. Appl. No. 2016/0151203 describes various PI designs, including a one-piece configuration, a two-part configuration, and a liquid interface two-part configuration. U.S. Pat. No. 9,089,401 describes a PI which includes, among other things, a connector that couples the PI to the laser optical system and is configured to accommodate adjustment of the contact element of the PI, where the connector may include a flexible element, an elastic element, a magnetic coupling element, a vacuum-suction element, a gravitational connector, a frictional connector or a viscous connector.

Many existing PIs use vacuum force to couple to the eye and stabilize the eye during the surgical procedure. Many existing PIs attach to the laser system via mechanical means, such as twist-to-lock, one-way slide, etc. A PI may be formed of a single component, or multiple components that are joined together during the docking process (i.e., the procedure of engaging the eye with the laser system using the PI). With those PIs that are comprised of multiple pieces, it can be difficult to join the pieces together especially if one portion is already in contact with the patient and the other connected to the laser system.

SUMMARY

Embodiments of the present invention are directed to a patient interface device and related method that substantially obviate one or more of the problems due to limitations and disadvantages of the related art.

An object of the present invention is to provide a patient interface that has a simple construction and is easy and convenient to use.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve these and/or other objects, as embodied and broadly described, an embodiment of present invention provides a patient interface device for coupling an eye of a patient to an ophthalmic surgical laser system, which includes: a hollow shell formed of a rigid material and defining an interior space, the shell having an upper rim and a lower portion; a transparent applanation lens disposed inside of and fixedly mounted to the lower portion of the hollow shell; and a flexible skirt having a circular shape, the flexible skirt being affixed to and extending downwardly from a lower end of the lower portion of the shell, wherein a lower rim of the flexible skirt is located below the applanation lens, wherein the lower portion of the shell defines one or more through channels in a region between the applanation lens and a side wall of the lower portion, to provide air communication between the interior space of the shell above the applanation lens and a space which is located below the applanation lens and encircled by the flexible skirt.

In another aspect, an embodiment of present invention provides a system for delivering a laser beam from an ophthalmic surgical laser system to a patient's eye, which includes: a patient interface device, including: a hollow shell formed of a rigid material and defining an interior space, the shell having an upper rim and a lower portion; a transparent applanation lens disposed inside of and fixedly mounted to the lower portion of the hollow shell; and a flexible skirt having a circular shape, the flexible skirt being affixed to and extending downwardly from a lower end of the lower portion of the shell, wherein a lower rim of the flexible skirt is located below the applanation lens, wherein the lower portion of the shell defines one or more through channels in a region between the applanation lens and a side wall of the lower portion, to provide air communication between the interior space of the shell above the applanation lens and a space which is located below the applanation lens and encircled by the flexible skirt; a laser delivery system coupled to the ophthalmic surgical laser system, including: a downwardly facing surface; and a patient interface mounting block protruding downwardly from the downwardly facing surface, the patient interface mounting block including a lower portion having an optical window near its bottom for delivering a laser beam generated by the ophthalmic surgical laser system, the patient interface mounting block defining an air channel inside the block, a first end of the air channel being open on an exterior of the block, and a second end of the air channel being configured to be connected to a vacuum source; and a magnetic mechanism for coupling the patient interface device to the laser delivery system, comprising a first part and a second part, one of the first and second parts being a magnet and another one of the first and second parts being either a magnet or a material attracted to magnets, wherein the first part is incorporated in the patient interface device and the second part is incorporated in the laser delivery system, wherein the first and second parts are located adjacent to each other when the patient interface device is coupled to the laser delivery system, wherein when the patient interface device is coupled to the laser delivery system, the patient interface mounting block is accommodated inside the shell of the patient interface device with an air gap defined between the shell and the patient interface mounting block, the air gap extending continuously between the first end of the air channel of the patient interface mounting block and the one or more through channels of the lower portion of the shell of the patient interface, and the upper rim of the patient interface is in contact with the downwardly facing surface of the laser delivery system to form a seal.

In another aspect, an embodiment of present invention provides a method for the system of claim 9 to couple the ophthalmic surgical laser system to the patient's eye, which includes: manually placing the patient interface device on the eye, wherein the flexible skirt of the patient interface device contacts the eye; while manually holding the patient interface device, moving the laser delivery system to a position above the patient interface device and aligned with the patient interface device; lowering the laser delivery system until the upper rim of the patient interface device is in contact with the downwardly facing surface of the laser delivery system, whereby the magnetic mechanism generates a magnetic force to hold the patient interface device on the laser delivery system; and applying a vacuum to the air channel of the patient interface mounting block, whereby a vacuum is generated in the air gap between the shell and the patient interface mounting block to hold the patient interface device to the laser delivery system, and whereby the vacuum is communicated to a space enclosed by the applanation lens, the flexible skirt and the eye to hold the eye to the patient interface device.

It is to be understood that both the foregoing general description and the following detailed description are exemplary and explanatory and are intended to provide further explanation of the invention as claimed.

DETAILED DESCRIPTION OF PREFERRED EMBODIMENTS

Embodiments of the invention provide an apparatus and related method for interfacing an ophthalmic surgical laser system with a patient's eye using a single-piece patient interface (PI). The PI includes a hollow shell, with an applanation lens and a flexible skirt located at the bottom of a cone shaped portion of the shell. Through channels are formed between the applanation lens and the side wall of the cone shaped portion to connect the spaces above and below the applanation lens. When the PI is coupled to the laser delivery system and the eye, the upper rim of the shell forms a seal with a downwardly facing surface of the laser delivery system, and the flexible skirt forms a seal with the eye. A vacuum is applied to the interior of the shell via a vacuum port which is located in the laser delivery system and opens to the interior of the shell, and the vacuum is communicated through the through channels around the applanation lens to the space below the applanation lens, i.e. the space enclosed by the applanation lens, the skirt and the eye. The vacuum securely holds the PI to both the laser delivery system and the eye. A magnetic mechanism is also provided to hold the PI shell to the laser delivery system to aid the eye docking process.

A PI and a laser delivery system according to embodiments of the present invention are described in more detail with reference to FIGS. 1-6.

Figure 1:
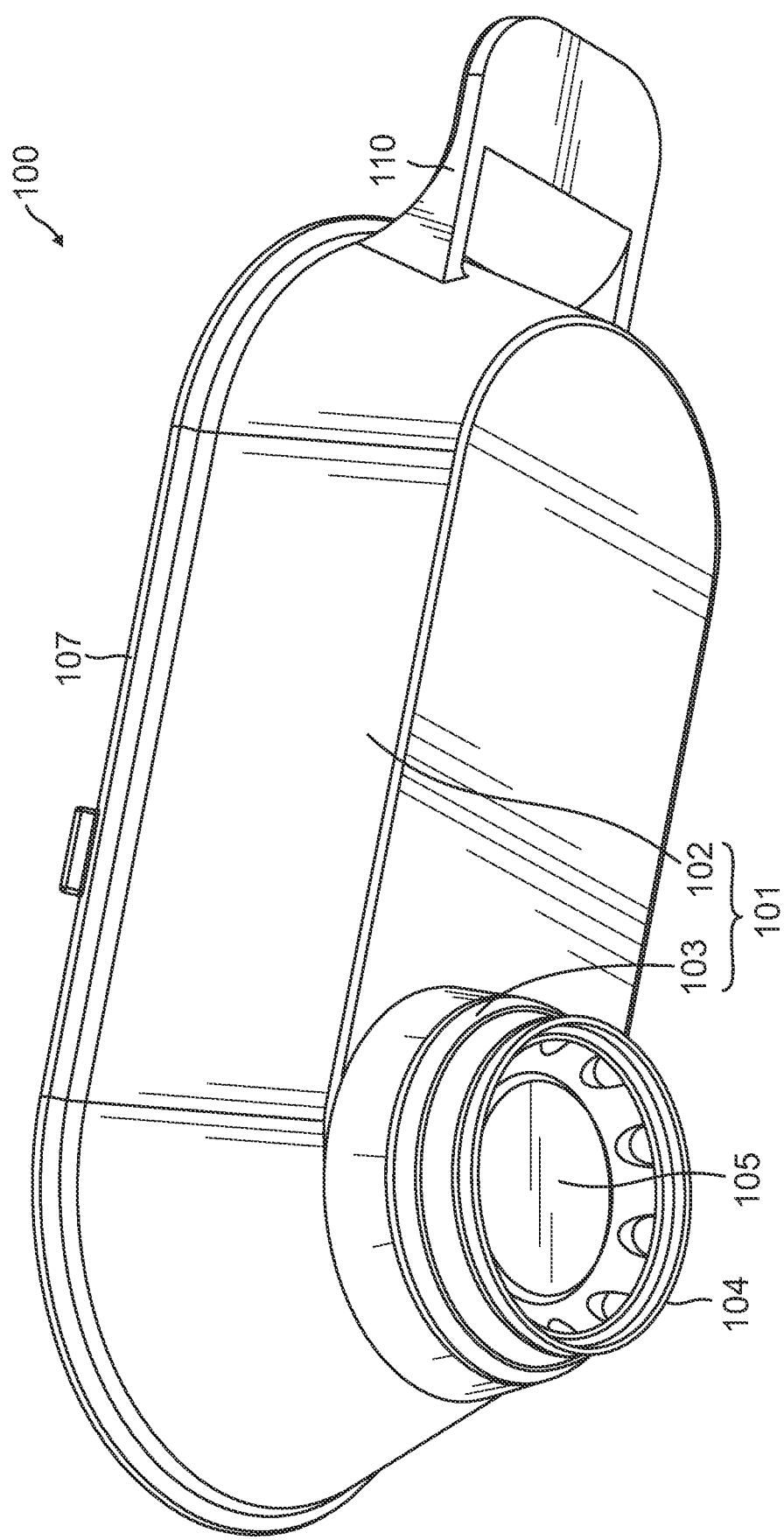
FIG. 1 is a bottom perspective view of a patient interface (PI) device according to an embodiment of the present invention.
Figure 2:
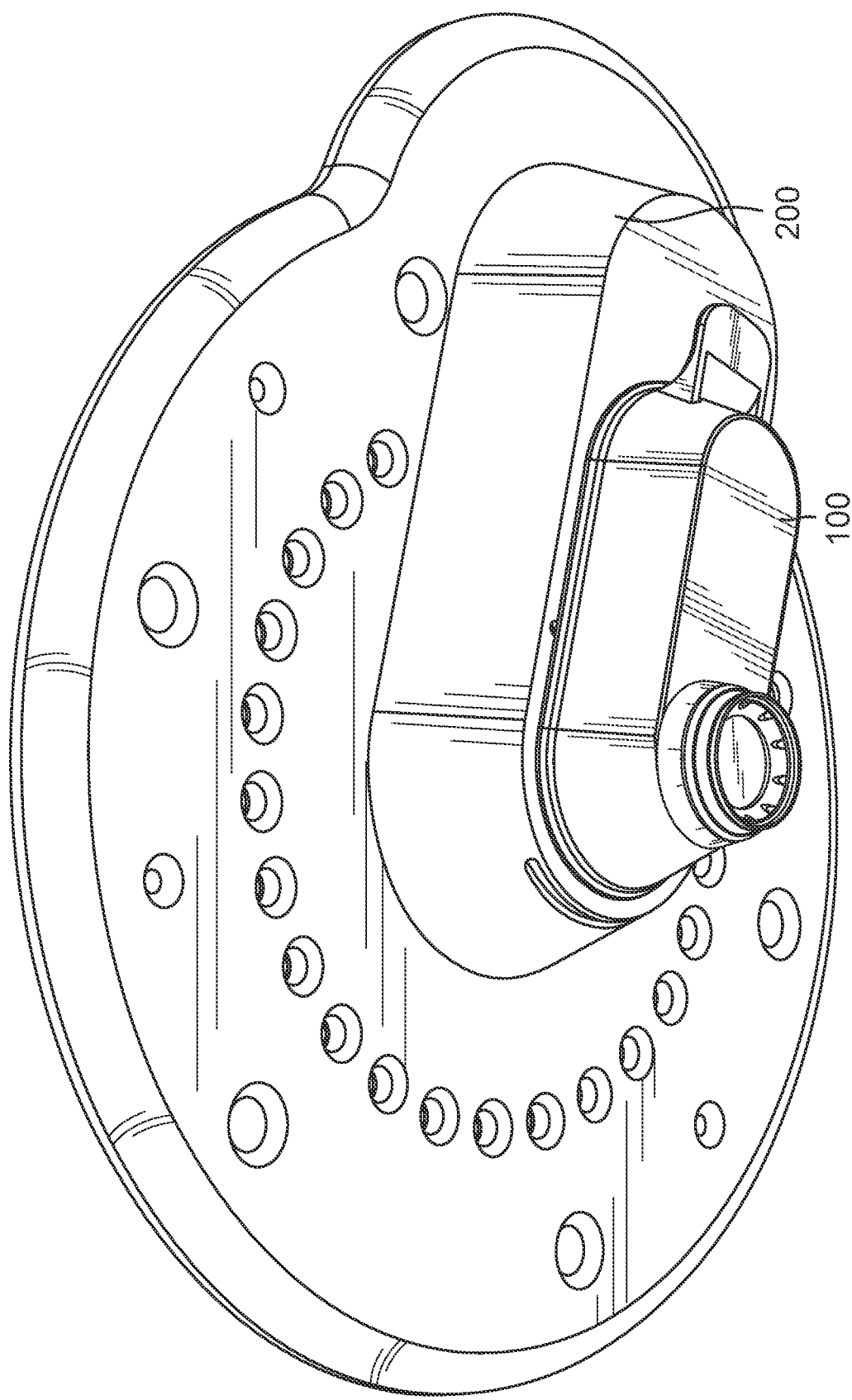
FIG. 2 is a bottom perspective view showing the PI coupled to a laser delivery system according to an embodiment of the present invention.
Figure 3:
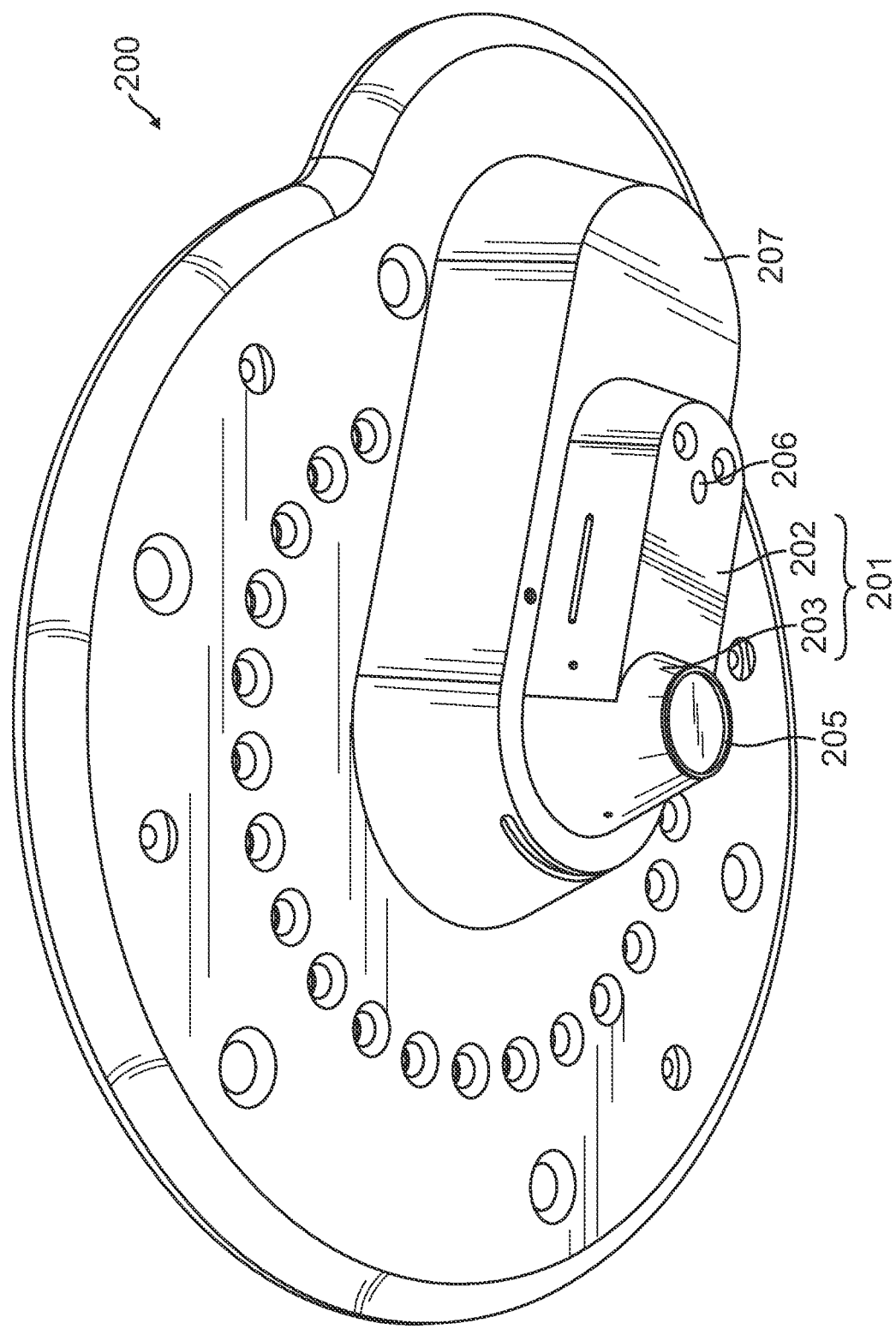
FIG. 3 is a bottom perspective view of the laser delivery system.
Figure 4:
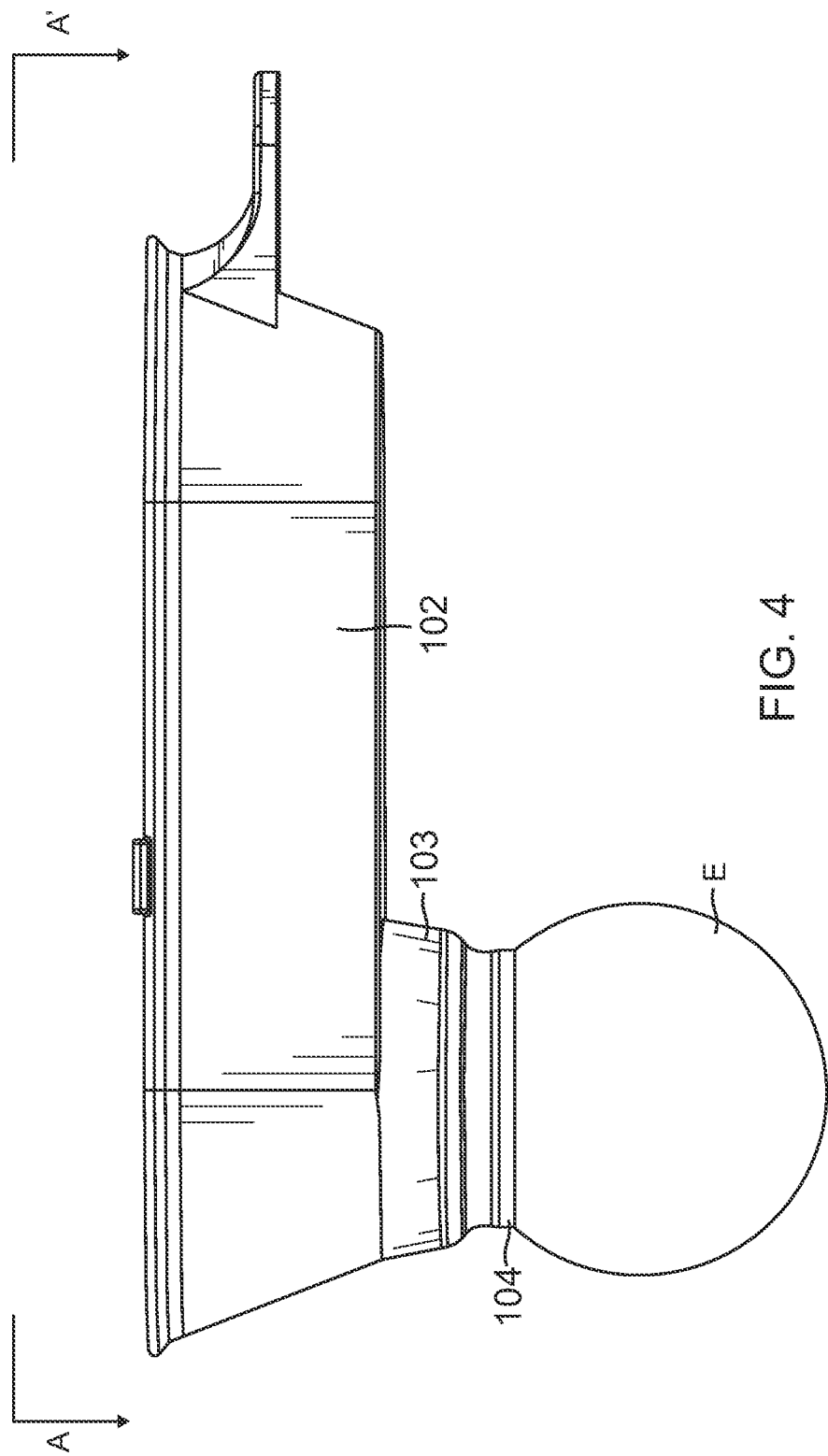
FIG. 4 is a side elevation view showing the PI coupled to the eye.
Figure 5:
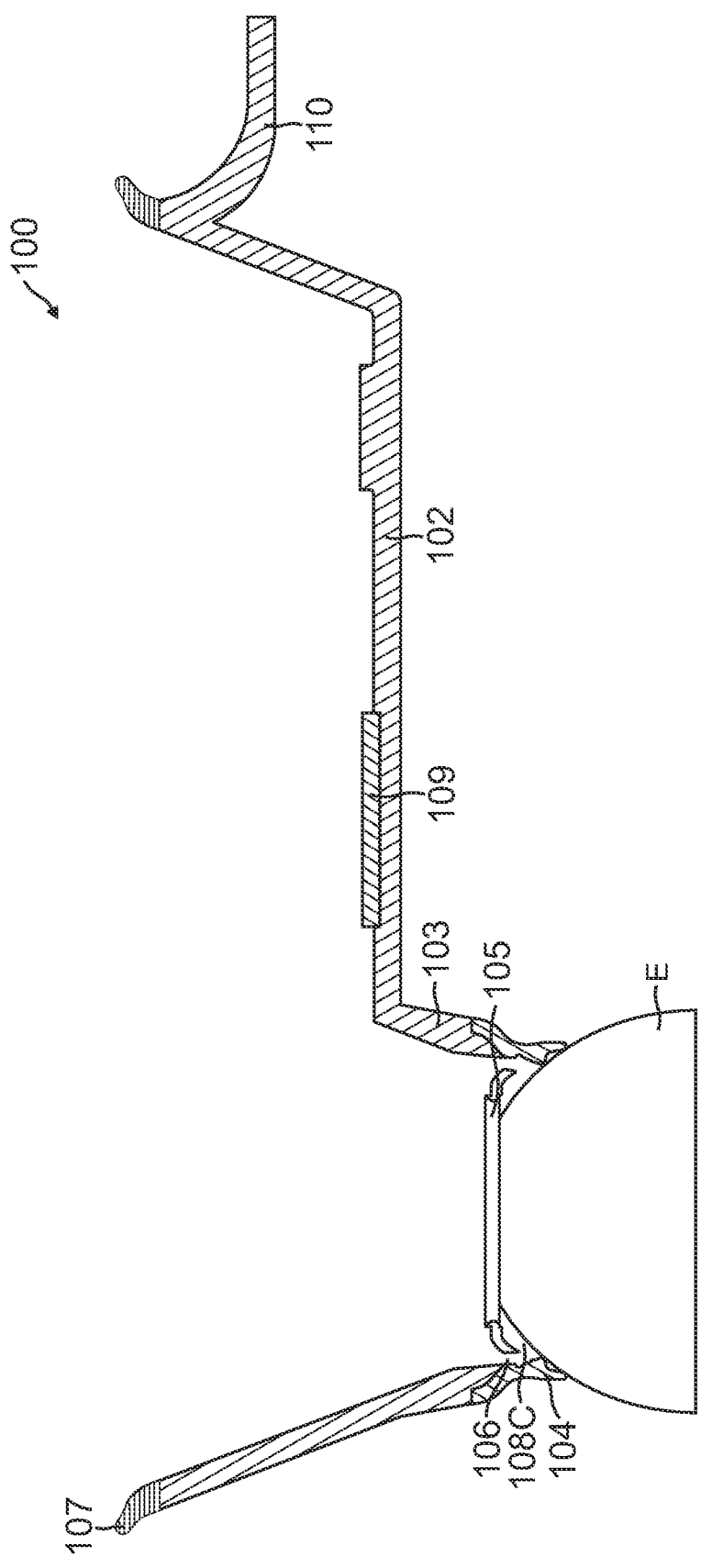
FIG. 5 is a sectional view of the PI coupled to the eye.
Figure 6:
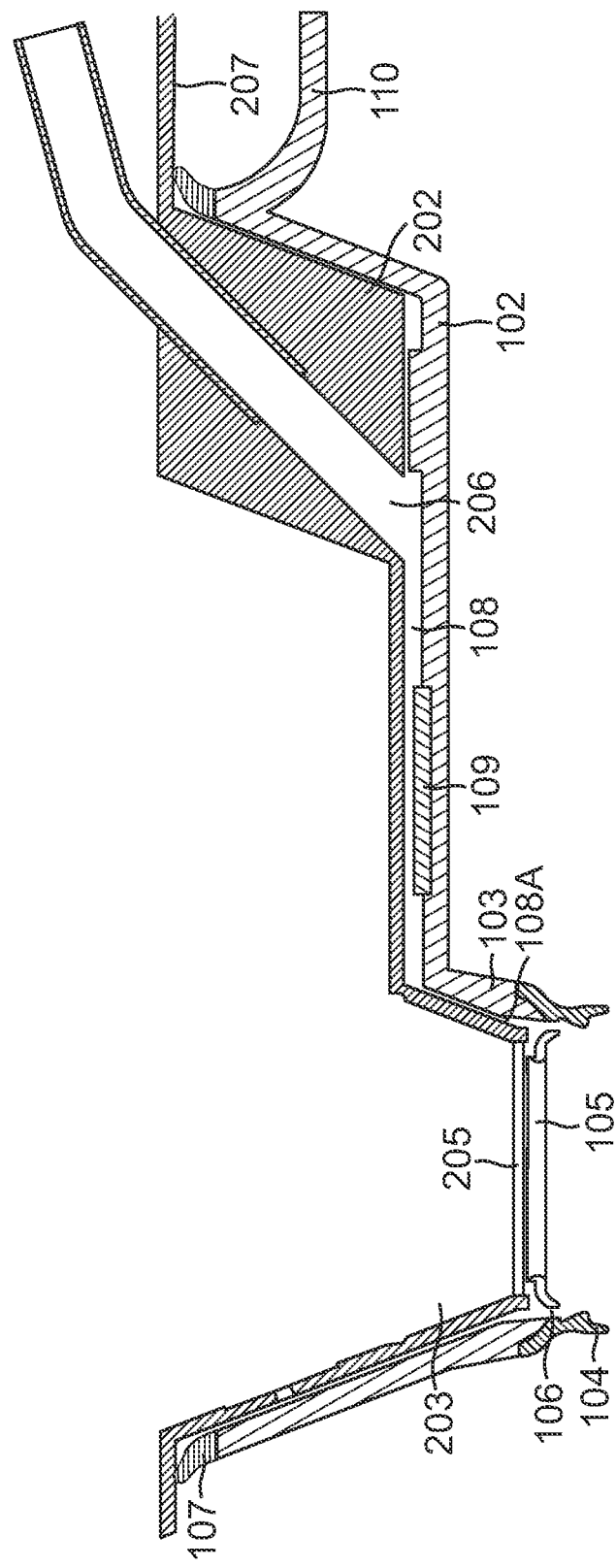
FIG. 6 is a sectional view of the PI and the laser delivery system coupled to each other.

As shown in FIG. 1 (bottom perspective view), the PI 100 is a single piece component, which is to be coupled at its upper side to the lower end of a laser delivery system of a laser system, and coupled at its lower side to the patient's eye E via a flexible sealing skirt. FIG. 2 (bottom perspective view) shows the PI 100 coupled to the laser delivery system 200. FIG. 3 (bottom perspective view) shows the laser delivery system 200 without the PI. FIG. 4 is a side elevation view showing the PI 100 coupled to the patient's eye E. FIG. 5 is a sectional view of the PI 100 coupled to the eye E, and FIG. 6 is a sectional view of the PI 100 and the laser delivery system 200 coupled to each other. The sections in FIGS. 5 and 6 are cut in a vertical direction indicated by arrows A-A' of FIG. 4 along a center plane of the PI.

As shown in FIGS. 1-6, the PI 100 has a hollow shell 101 which includes an upper portion 102 and a lower portion 103. The upper portion 102 may have any suitable shape; in the illustrated embodiment, the upper portion 102 has the shape of an elongated tub with a flat bottom. The lower portion 103 preferably has the shape of an upside-down truncated cone, but it may also have a cylindrical shape, or other suitable shapes. In the illustrated embodiment, the lower portion 103 is located at one end of the elongated upper portion 102, but other configurations may also be used. For convenience, in this disclosure, the lower portion 103 of the PI shell 101 is referred to as the cone portion and the upper portion 102 is referred to as the tub portion.

The lower end of the cone portion 103 includes a circular shaped flexible skirt 104. A transparent member 105, referred to as an applanation lens, is disposed inside and fixedly mounted to the cone portion 103 of the shell. The applanation lens 105 may have a planar (horizontally oriented) or curved bottom surface, which is located above the lower rim of the flexible skirt 104. When the PI 100 is coupled to the patient's eye E, the applanation lens 105 contacts and applanates the cornea of the eye, and the flexible skirt 104 contacts the eye's surface (e.g. the sclera) to create a seal between the PI and the eye.

In a ring shaped region between the applanation lens 105 and the side wall of the cone portion 103, one or more through channels 106 are formed to connect the interior space of the hollow PI shell 101 above the applanation lens with a space 108C which is located below the applanation lens 105 and encircled by the flexible skirt 104, i.e. a space enclosed by the applanation lens, the flexible skirt and the surface of the eye E when the PI 100 is coupled to the eye, to allow fluid (including air) communication between the two spaces.

The lower end of the laser delivery system 200 has a PI mounting block 201 that protrudes downwardly from a generally flat and horizontally oriented lower surface 207. The PI mounting block 201 has a size and shape that can be accommodated inside the hollow interior of the PI shell 101 when the PI 100 is coupled to the laser delivery system 200. The PI mounting block 201 includes a laser delivery portion 203 having an upside-down truncated-cone shape or a cylindrical shape, or other suitable shape, with an optical window 205 at its bottom from which the laser beam of the laser system exits. The optical window 205 may be the surface of an optical element such as a lens, a prism, etc., of the laser delivery system 200. When the PI 100 is coupled to the laser delivery system 200, the optical window 205 is located directly above the applanation lens 105 of the PI 100 for delivering the laser beam into the eye.

When the PI 100 is coupled to the laser delivery system, the upper rim 107 of the tub portion 102 of the PI shell 101 is in contact with the lower surface 207 of the laser delivery system 200 to create an air tight seal. The upper rim (upper seal) 107 of the PI shell 101 may include a flexible material, and/or have a flange shape, to facilitate the sealing with the laser delivery system 200.

In one embodiment, an upper portion 202 of the PI mounting block 201 and a part of the tub portion 102 of the PI shell 101 have a mating shape in a horizontal cross-section so that when the PI 100 is couple to the laser delivery system 200 with the PI mounting block 201 contained inside the shell, the PI 100 is prevented from moving horizontally relative to the laser delivery system 200. This facilitates the alignment of the laser beam from the optical window 205 relative to the applanation lens 105 and thus the alignment of the laser beam relative to the eye. In an alternative embodiment, a groove is provided on the lower surface 207 of the laser delivery system 200, the groove having a shape that mates with the upper seal 107 of the PI 100, so that when the PI is coupled to the laser delivery system, the upper seal falls in the groove and the PI is prevented from moving horizontally.

The size and shape of the hollow PI shell 101 and of the PI mounting block 201 are such that a continuous air gap 108 is present between them. A part of the air gap 108A extends between the laser delivery portion 203 of the PI mounting block 201 and the cone portion 103 of the PI shell 101, so that the one or more through channels 106 located around the applanation lens 105 are open to the air gap. For example, the air gap 108A may extend between the side walls of the laser delivery portion 203 and the cone portion 103, and/or between the optical window 205 of the laser delivery portion 203 and the applanation lens 105.

An air channel 206 is provided inside the PI mounting block 201 and is open to the air gap 108 between the PI mounting block and the PI shell 101. The other end of the air channel 206 is coupled via a pipe or other means to a vacuum source or suction pump, so that the air channel can functions as a vacuum port to create a vacuum in the air gap. In the illustrated embodiment, the opening 206A of the vacuum port 206 is located on the bottom of the upper portion 202 of the PI mounting block 201, and a part of the air gap 108 extends between the bottom surface of the upper portion 202 of the PI mounting block 201 and the flat bottom panel of the tub portion 102 of the PI shell 101.

A magnetic mechanism is provided to generate a magnetic attraction force between the laser delivery system 200 and the PI 100. The magnetic mechanism includes two parts, one being a magnet, the other being a piece of material that is attracted to magnets (e.g. a ferromagnetic or paramagnetic material such as steel and some other metals) or another magnet. The two parts are located respectively on the PI 100 and the laser delivery system 200 at respective locations that are adjacent to each other when the PI 100 is coupled to the laser delivery system 200. In one embodiment, as shown in FIGS. 5 and 6, a disk 109 made of a material that is attracted to magnets is affixed on the inside of the bottom panel of the tub portion 102, and the PI mounting block 201 includes a magnet located at or near the bottom of the upper portion 202 at a location adjacent to the disk 109 when the PI 100 is coupled to the laser delivery system 200. Alternatively, the disk 109 is a magnet, and a magnet or a material that is attracted to magnets is provided at the corresponding location of the upper portion 202 of the PI mounting block 201. The disk 109 may be embedded or adhered to the bottom panel of the tub portion 102, or it may be an integral part of the PI shell 101 (for example, the tub portion 102 or the bottom panel may be made of steel). In these embodiments, the two parts of the magnetic mechanism may be in direct contact with each other or have a small air gap between them when the PI 100 is coupled to the laser delivery system 200. Other spatial arrangements for the two parts may be employed, so long as they generate an adequate magnetic attraction force between the laser delivery system 200 and the PI 100.

In preferred embodiments, the PI shell 101 is formed of a rigid material such as rigid plastic, metal, etc., and the skirt 104 and the upper seal 107 are formed of flexible materials, preferably a compliant natural or synthetic polymer, such as silicone, flexible plastic, rubber, etc. The flexible skirt 104 and the upper seal 107 are affixed to the PI shell 101 in an air-tight manner by any suitable means such as adhesion, etc. The cone portion 103 and the tub portion 102 of the PI shell 101 are preferably formed integrally, e.g., by molding, overmolding, thermoforming, etc.

It should be noted that the design where the cone portion 103 of the PI shell 101 protrudes from the bottom of the tub portion 102 provides a clearance for the patient's face (e.g. bridge of the nose) to prevent possible interference when the PI is coupled to the eye. As stated earlier, the upper portion 102 of the PI shell may have other suitable shapes, so long as it can accommodate the PI mounting block and has an upper rim that can be sealed to a downwardly facing surface of the laser delivery system 200.

In operation, the coupling of the PI 100 to the laser delivery system 200 is accomplished by both the magnetic force generated by the magnetic mechanism and a vacuum sealing force generated by a vacuum in the air gap 108. The coupling of the PI 100 to the patient's eye E is accomplished by a vacuum sealing force generated by a vacuum in the space 108C enclosed by the skirt 104, the applanation lens 105 and the surface of the eye E. Because the space 108C is in fluid communication with the air gap 108, the same vacuum source generates the vacuum sealing force that seals the PI 100 to both the laser delivery system 200 and the eye E.

Figure 7:
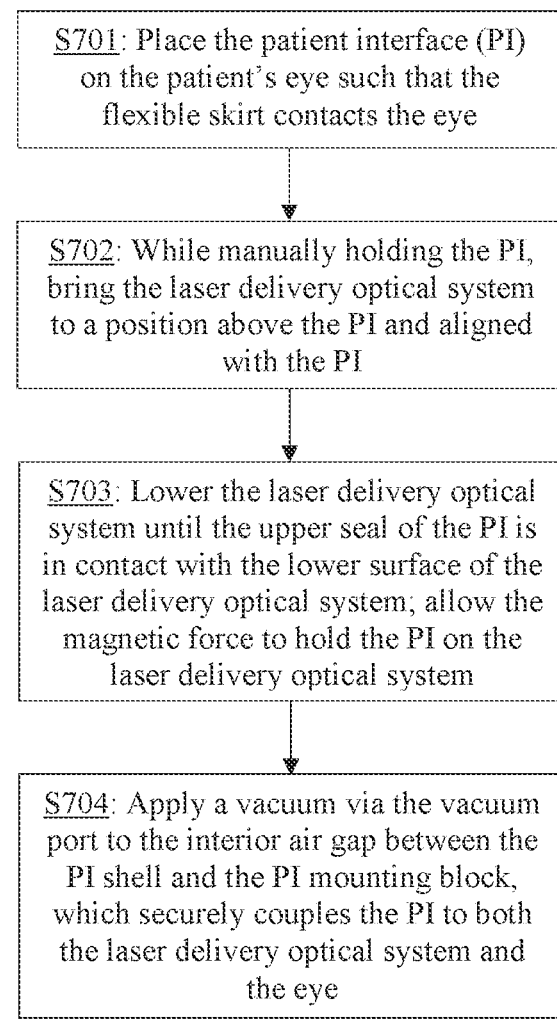
FIG. 7 schematically illustrates a method for coupling the patient's eye with the laser delivery system using the PI according to an embodiment of the present invention.

The eye docking process during surgery, i.e., the process of engaging the eye with the laser delivery system 200 using the PI 100, is described with reference to FIG. 7.

First, the surgeon places the PI 100 on the patient's eye (which faces upward) such that the flexible skirt 104 contacts the eye (e.g. the sclera) (step S701). The cornea of the eye may be applanated by the applanation lens 105 in this step. While manually holding the PI 100, the surgeon then brings the laser delivery system 200 to a position that is above the PI and approximately aligned with the PI (step S701). For example, the optical window 205 of the laser delivery system 200 is approximately aligned with the applanation lens 105, and the upper portion 202 of the PI mounting block 201 is approximately aligned with the tub portion 102 of the PI shell 101. The surgeon then lowers the laser delivery system 200, so that the PI mounting block 201 is lowered into the hollow space of the PI shell 101, until the upper seal 107 of the PI 100 is in contact with the lower surface 207 of the laser delivery system (step S703). At this time, the magnetic force generated by the magnetic mechanism operates to hold the PI 100 on the laser delivery system 200. During step S703, the magnetic mechanism allows the PI 100 to "snap" into place on the laser delivery system 200, and provides a well-defined tactile feel of proper attachment of the PI 100 to the system 200. Then, a vacuum is applied to the interior air gap 108 between the PI shell 101 and the PI mounting block 201 via the vacuum port 206 (step S704). The vacuum pressure securely couples the PI 100 to the laser delivery system 200. At the same time, through the one or more through channels 106 located around the applanation lens 105, the vacuum pressure is also applied to the space 108C enclosed by the applanation lens 105, the flexible skirt 104 and the surface of the eye E. This vacuum pressure securely couples the PI 100 to the eye. This completes the docking process. The vacuum is continuously applied throughout the laser surgery.

It is noted that the magnetic force generated by the magnetic mechanism only needs to temporarily hold the PI 100 to the laser delivery system 200 during docking. Therefore, only a moderate magnetic force is required, making it easy to remove the PI 100 from the laser delivery system 200 after the surgery. An optional handle 110 may be provided on the PI 100 for convenient handling of the PI.

No other coupling mechanisms beside the magnetic mechanism and the vacuum seal between the upper seal 107 and the lower surface 207 of the laser delivery system 200 are required to couple the PI 100 to the laser delivery system. No twisting or lateral sliding actions are required to couple the PI to the laser delivery system.

To summarize, the patient interface (PI) according to embodiments of the present invention is a single piece component that attaches to the laser delivery system first via a magnetic mechanism that allows it to "snap" into place, and then by a vacuum sealing force. The PI simplifies the docking process and reduces the time required for the laser system attachment and readiness. The magnetic mechanism also provides a well-defined tactile feel of proper attachment of the PI to the system. The integrated vacuum port requires no tubing attachment to the PI itself, which simplifies attachment and removal of the PI to and from the laser system, and also prevents vacuum tubing from interfering with the surgeon's work area. The elimination of vacuum tubing and associated fittings also reduces manufacturing cost of the PI.

The PI according to embodiments of the present invention can be used in various ophthalmic laser systems, including, without limitation, femtosecond lasers for flap cutters and laser cataract systems.

It will be apparent to those skilled in the art that various modification and variations can be made in the patient interface device and the laser delivery system as well as related methods of the present invention without departing from the spirit or scope of the invention. Thus, it is intended that the present invention cover modifications and variations that come within the scope of the appended claims and their equivalents.

What is claimed is:

1. A patient interface device for coupling an eye of a patient to an ophthalmic surgical laser system, comprising:
   a hollow shell formed of a rigid material and defining an interior space, the shell having an upper rim and a lower portion;
   a transparent applanation lens disposed inside of and mounted to the lower portion of the hollow shell; and
   a flexible skirt having a circular shape, the flexible skirt being affixed to and extending downwardly from a lower end of the lower portion of the shell, wherein a lower rim of the flexible skirt is located below the applanation lens,
   wherein the lower portion of the shell defines one or more through channels in a region between the applanation lens and a side wall of the lower portion, wherein each of the one or more through channels is open to and in air communication with both the interior space of the shell above the applanation lens and a space which is located below the applanation lens and encircled by the flexible skirt, wherein each of the one or more through channels is configured to communicate a vacuum to secure the patient interface device to the ophthalmic surgical laser system and to the eye.

2. The patient interface device of claim 1, wherein the upper rim of the shell includes a flexible material.

3. The patient interface device of claim 2, wherein the flexible material of the upper rim is a compliant natural or synthetic polymer.

4. The patient interface device of claim 1, wherein the flexible skirt is made of a compliant natural or synthetic polymer.

5. The patient interface device of claim 1, wherein the lower portion of the shell has a shape of an upside-down truncated cone.

6. The patient interface device of claim 5, wherein the shell further includes an upper portion, wherein an upper rim of the upper portion is the upper rim of the shell, and wherein the lower portion of the shell extends downwardly from the upper portion.

7. The patient interface device of claim 6, further comprising a magnet or a piece of material that is attracted to magnets, affixed to the upper portion of the shell.

8. The patient interface device of claim 1, wherein the shell includes a magnet or a piece of material that is attracted to magnets.

* * * * *